(12) United States Patent
Tenaglia et al.

(10) Patent No.: US 7,906,745 B2
(45) Date of Patent: Mar. 15, 2011

(54) BEND BAR QUALITY CONTROL METHOD FOR LASER SHOCK PEENING

(75) Inventors: Richard D. Tenaglia, Columbus, OH (US); Allan H. Clauer, Worthington, OH (US); Jeff L. Dulaney, Dublin, OH (US); David F. Lahrman, Powell, OH (US); Steve Toller, Dublin, OH (US)

(73) Assignee: LSP Technologies, Inc., Dublin, OH (US)

( * ) Notice: Subject to any disclaimer, the term of this patent is extended or adjusted under 35 U.S.C. 154(b) by 919 days.

(21) Appl. No.: 11/009,123

(22) Filed: Dec. 10, 2004

(65) Prior Publication Data

US 2006/0021409 A1 Feb. 2, 2006

Related U.S. Application Data

(60) Provisional application No. 60/528,569, filed on Dec. 10, 2003.

(51) Int. Cl.
*B23K 26/00* (2006.01)
(52) U.S. Cl. .............. 219/121.85; 219/121.6; 219/121.83
(58) Field of Classification Search .............. 219/121.85, 219/121.6, 121.83; 148/903; 72/53
See application file for complete search history.

(56) References Cited

U.S. PATENT DOCUMENTS

| | | | | |
|---|---|---|---|---|
| 2,350,440 A | * | 6/1944 | Almen | 73/11.02 |
| 2,620,838 A | * | 12/1952 | Huyett et al. | 269/240 |
| 3,695,091 A | * | 10/1972 | Smith | 73/11.02 |
| 4,102,176 A | * | 7/1978 | Fuchs | 73/11.02 |
| 4,329,862 A | * | 5/1982 | Harburn et al. | 72/53 |
| 5,297,418 A | * | 3/1994 | Champaigne | 73/11.02 |
| 5,741,559 A | * | 4/1998 | Dulaney | 427/554 |
| 5,780,714 A | * | 7/1998 | Champaigne | 73/1.79 |
| 5,877,405 A | * | 3/1999 | Champaigne | 73/11.02 |
| 5,951,790 A | * | 9/1999 | Mannava et al. | 148/510 |
| 6,130,400 A | * | 10/2000 | Rockstroh | 219/121.6 |
| 6,183,882 B1 | * | 2/2001 | Mannava et al. | 428/614 |
| 6,289,713 B1 | * | 9/2001 | Champaigne | 73/1.79 |
| 6,483,578 B1 | * | 11/2002 | Clauer et al. | 356/213 |
| 6,512,584 B1 | * | 1/2003 | O'Loughlin et al. | 356/388 |
| 6,568,239 B1 | * | 5/2003 | Champaigne | 73/1.04 |

* cited by examiner

*Primary Examiner* — M. Alexandra Elve
(74) *Attorney, Agent, or Firm* — Benjamen E. Kern (57) ABSTRACT

A bend bar is available for use in a quality control test for testing for a consistency of residual stress effects in a particular material using a given a laser peening process. The bar is composed of the particular material to be tested and has a bar length and a bar thickness. The particular material has a characteristic maximum stress penetration depth for compressive residual stresses that can be formed in using the given laser peening process. The bar thickness is chosen so as to be at least twice the characteristic maximum stress penetration depth. The bar has a test surface that extends parallel to the bar length and perpendicular to the bar thickness. After forming a spot pattern on the test surface using the given laser peening process, the deflection generated in the bar due to the compressive residual stresses induced by laser peening can then be measured and used as a quality control measurement.

20 Claims, 5 Drawing Sheets

BEND BAR QUALITY CONTROL METHOD FOR LASER SHOCK PEENING

CONTINUATION DATA

This application claims priority from U.S. Provisional Patent Application No. 60/528,569, filed on Dec. 10, 2003, the disclosure of which is herein explicitly incorporated by reference.

BACKGROUND OF THE INVENTION

1. Field of the Invention

The present invention relates to an improved quality control method for laser shock processing in which the consistency of residual stress effects produced thereby are monitored and more specifically, relates to a quality control method which employs bend bars for such testing.

2. Description of the Related Art

Laser peening creates deep compressive residual stresses in the surface of a metal part being treated. Such compressive stresses beneficially improve the fatigue strength, fatigue life, fretting fatigue resistance, and stress corrosion cracking resistance of components.

There are problems associated with monitoring and verifying the level of residual stresses developed in a part. Residual stress measurements may be made using X-Ray diffraction (XRD) measurements or compliance methods (e.g., hole drilling, strain gauging with sectioning, etc.), but such methods are generally destructive in that samples must be sacrificed for testing. In addition, these tests are time consuming, and the results are not available until after all the parts are processed. During laser peening operations, it is desirable to perform periodic quality checks to ensure that the application of laser peening is consistent and reproducible. Toward this goal, it is useful to have a test specimen that may be processed quickly and economically to assess the status of the laser peening operation. Such a test specimen and method may also be used for process development and optimization.

Such a test specimen that has been used to ascertain the extent of traditional shot peening coverage is a small, thin steel strip known as an Almen gage or Almen strip. There are three different thicknesses of these strips, 0.040, 0.060, and 0.090 inches thick denoted as N, A, and C, respectively. The selection of the strip is dependent upon the intensity of the shot peen process to be used on the components. The thinner strips are used for relatively low intensity shot peening, while the thicker strips are used for high intensity shot peening. The strips are shot peened on one side causing the strip to bow toward the peened surface as the residual stress increases. As such, the extent of bowing at the center of the strip is a relative measure of the induced compressive residual stress and the extent of coverage. The bowing is induced in the strip because of the compressive residual stresses induced to a depth of nominally 0.005 inches near the surface of the strip. The use of Almen strips to monitor laser peening has been attempted, but the results have been disappointing with considerable data scatter and poor reproducibility.

A specific drawback with the use of a standard steel Almen strip for use with laser peening is the limited thickness thereof. The thickest commercially available Almen strips, C strips, are only 0.090 inches in thickness. Since the compressive residual stresses generated with laser peening are often greater than 10 times deeper than those generated with shot peening, the residual compressive stress profiles produced in steel by laser peening can extend to 0.040 inches to 0.060 inches deep, thereby extending past the mid-plane thickness of the steel strip. It has been realized that when the compressive residual stress profile extends past the mid-plane of the strip, there would be a reverse bending component driven by the compressive residual stresses extending past the mid-thickness of the strip. In this case, there would not be a single strip arc-deflection value for each laser peening intensity. This characteristic of the Almen strips make them unsuitable for monitoring laser shock processing.

Clauer® strips have been developed as a means to monitor laser peening operations. These are thin aluminum alloy 6061-T6 strips (100 mm×6 mm×t), where the thickness is selected within the range of 0.9 to 2.0 mm, depending upon the laser peening conditions being applied. Clauer strips are one-shot, mechanical gages that measure the impulse generated by the laser pulse. The strips are gripped at one end, and the laser pulse hits on the opposite end. The intensity of the laser pulse is related to the amount of bending in the Clauer® strip.

While the Clauer® strips are relatively inexpensive and easy to use, the amount of bending is not necessarily a true measure of the residual stresses induced in the part, but rather a measure of the force applied to the tip of the strip. Alignment of the gage is rather critical, and moderate scatter in the data can occur depending on a number of factors. As such, Clauer® strips are probably best used as a "go-no go" semi-quantitative test rather than as a direct indicator of residual stresses imparted to the workpiece.

What is needed in the art is a reliable and economical quality control tool to measure the effects of compressive residual stresses developed during a laser peening process to ensure product consistency in laser peened components during production operations.

SUMMARY OF THE INVENTION

The present invention provides a quality control method for laser shock processing involving the use of bend bars which have a minimum thickness requirement. As a result, compressive residual stresses formed therein during testing do not inadvertently create an opposing torque, which will tend to reverse the bending otherwise driven by the surface compressive stresses induced by the laser shock processing. Further, the bend bars employed in the present invention are also advantageously long enough so as to produce bend bar deflection or bowing levels that are quickly and easily measured and that are sensitive to variations in laser peening parameters.

The present invention, in one form thereof, comprises a quality control method of representing a laser peening intensity with a particular material. The method includes the steps of providing a laser peening system, selecting the process parameters, providing a test object, choosing a test surface, laser peening a spot pattern along the test surface, and measuring the deflection. The laser peening system provided is configured for laser peening an object, a laser peening system having a plurality of selectable process parameters associated therewith. The process parameters for the laser peening system are then selected. The test object provided is composed of the particular material, the test object being a bend bar. The bend bar has a bar thickness, bar width, and bar length, and the test material has a characteristic maximum stress penetration depth for compressive residual stresses creatable by laser peening the test material using the laser peening system. The laser peening system is set to operate under the selected process parameters. The bar thickness is chosen so as to be at least twice the characteristic maximum stress penetration depth. A test surface on the bend bar is chosen, the test surface being parallel to the bar length and perpendicular to the bar thickness. A spot pattern is laser peened along the test surface of the bend bar. The laser peening is performed using the laser peening system set to operate under the selected process parameters. The laser peening causes compressive residual stresses to form within the bend bar. The compressive residual stresses extend from the test surface and into the bend bar, the compressive residual stresses effectively inducing bending and a resulting deflection of the bend bar. The deflection in the bend bar is measured, the measured deflection being usable as a quality control measurement represented by the effect of the laser peening intensity upon the particular geometry and material composition of the bend bar.

The present invention, in another form thereof, comprises a bend bar for use in a quality control test for testing a consistency of residual stress effects produced in a particular material by a given laser peening process. The bend bar includes a bar composed of a particular material. The bar has a bar length, bar width, and bar thickness, and the particular material has a characteristic maximum stress penetration depth for compressive residual stresses formable therein by the given laser peening process. The bar thickness is chosen so as to be at least twice the characteristic maximum stress penetration depth. The bar has a test surface, the test surface extending parallel to the bar length and perpendicular to the bar thickness.

An advantage of the present invention is that the bend bar quality control test specimen and method provide a reliable and economical quality control tool for measuring the effects of compressive residual stresses in order to ensure consistency in laser peening operations.

Another advantage of the present invention is that the bend bar thickness can be chosen within a range that provides much more consistency in deformation results than is possible with conventional thin specimens.

Yet another advantage of the present invention is that the bar length can be chosen so as to facilitate production of a readily measurable deflection (i.e., at least about 0.010 inches) within the bend bar upon performing the given laser peening process thereon.

An even yet further advantage of the present invention is that the bend bar width can be chosen so as to facilitate the application of a particular laser peen pattern that is repetitive of the pattern being applied to the production components.

An even yet further advantage of the present invention is that the bend bar width can be chosen to facilitate an optimization in bend bar deflection considering the effects of bar material, bar geometry, and the laser peen pattern and intensity.

An even yet further advantage of the present invention is that the deflection in the bend bar can be quickly and easily measured using a simple dial gauge indicator, making the bend bar quality control method easily adaptable to laser peening operations.

An additional advantage of the present invention is that the bend bar quality control specimen for laser peening may be made using any material and dimensions suitable for representing a component that is being laser peened. For example, the bend bar concept could be used on cylindrical rods or other cross sectional shapes to represent components with similar geometries.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates at least one preferred embodiment of the invention, in one form, and such exemplification is not to be construed as limiting the scope of the invention in any manner.

DETAILED DESCRIPTION OF THE INVENTION

Figure 1:
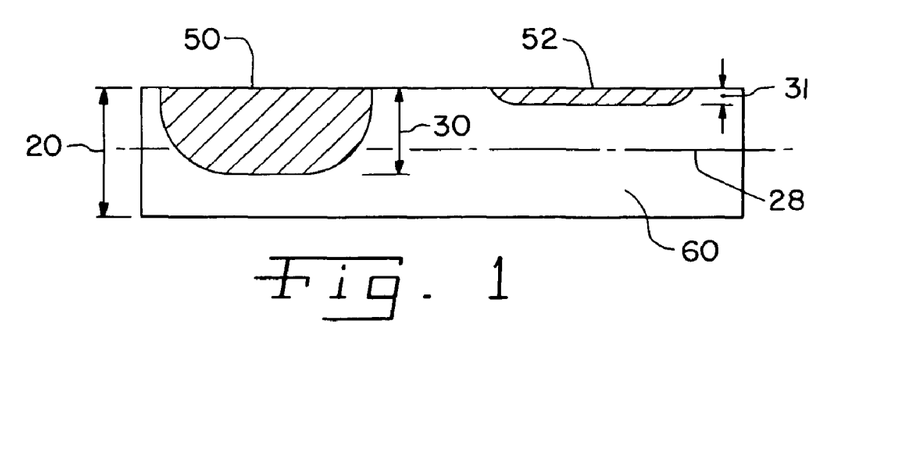
FIG. 1 is a schematic side view of an Almen strip of the prior art that has been exposed to laser peening in one location and conventional metal shot peening in another location.

Referring now to the drawings, FIG. 1 shows an Almen strip 60 of thickness 20 having a laser peened surface 50 and a shot peened surface 52. The depth of compressive stress 30 under the laser peened surface extends beyond the mid-thickness plane 28 of the Almen strip 60, while the shot peened compressive stress depth 31 is far from the mid-thickness plane. A problem arises at laser peened surface so in that it is necessary that the depth 30 does not extend beyond the mid-thickness plane 28 of the Almen strip 60 to achieve consistent deflection measurements for process monitoring.

Figure 2:
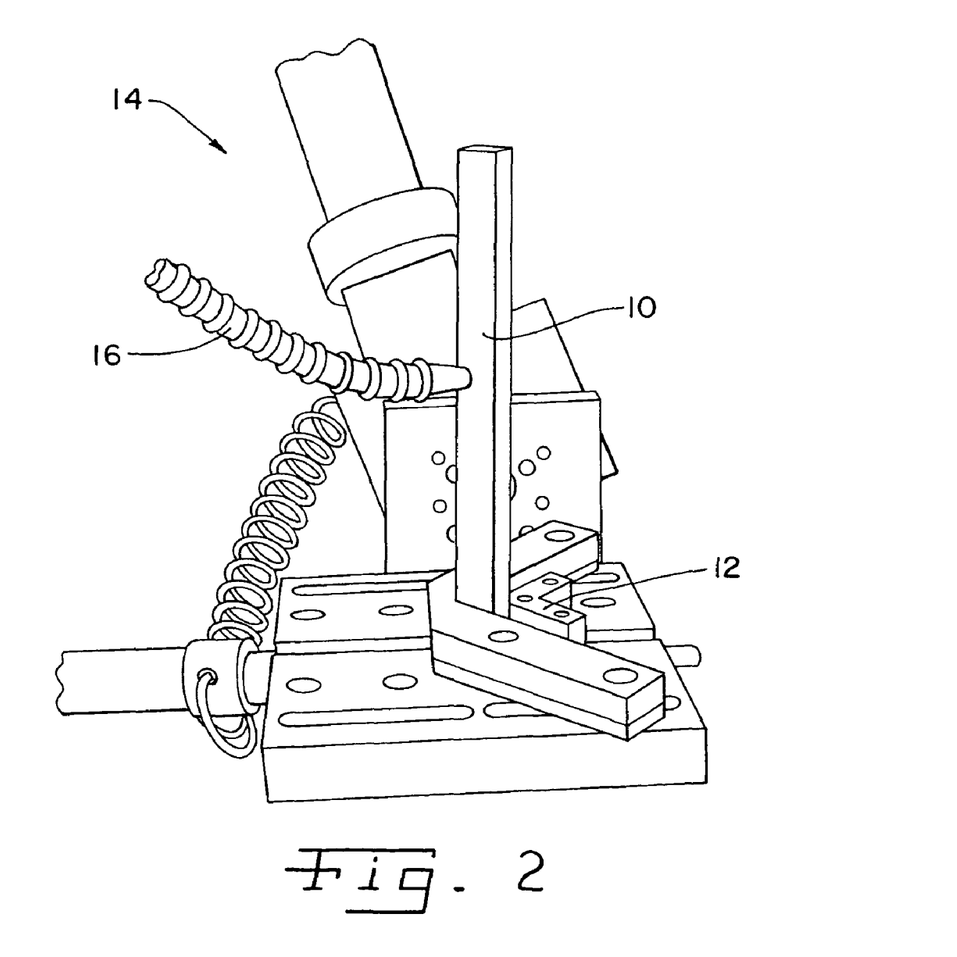
FIG. 2 is perspective view of a quality test system of the present invention featuring a bend bar positioned in a fixture for laser peening with a laser peening apparatus.

In FIG. 2, there is shown a bend bar 10 of the present invention for use in testing for the consistency of residual stress effects created during laser peening. Bend bar 10 is shown, mounted in a vise fixture 12, for treatment with a laser peening apparatus 14. The illustrated version of laser peening apparatus 14 (FIGS. 4A and 4B) includes a laser mechanism 15, transparent overlay delivery means 16, and an opaque overlay apparatus 40.

Figure 3:
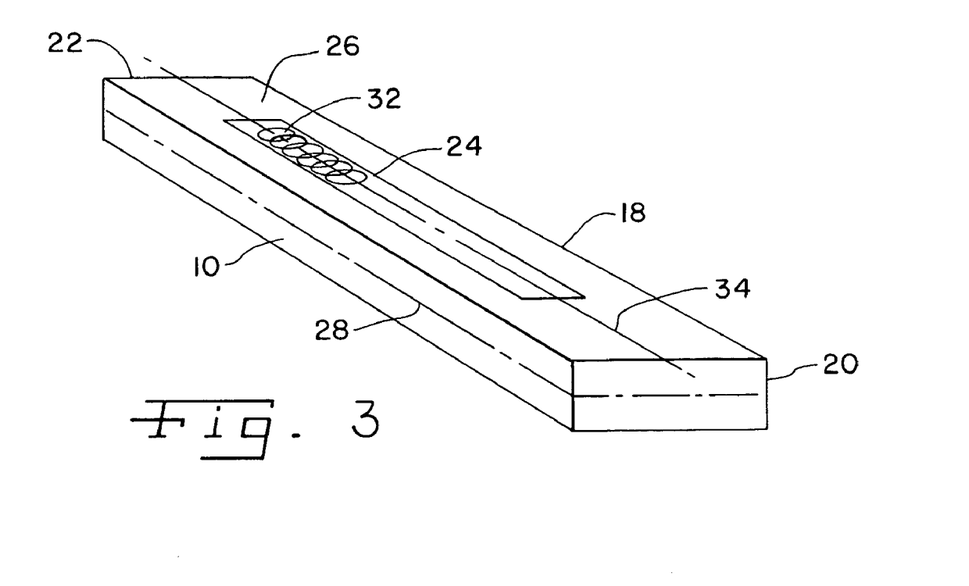
FIG. 3 is a perspective view of a laser-peened bend bar of the present invention primarily showing the test surface thereof.

Bend bar 10, a treated version of which is shown in FIG. 3, has a bar length 18, a bar thickness 20, and bar width 22. Bend bar 10, as seen in FIG. 3, has a test area 24 on test surface 26 within which laser peening has been performed. Test surface 26 is chosen so as to be parallel to bar length 18 and perpendicular to bar thickness 20. Bar 10 is composed of a particular material (e.g., a steel alloy, an aluminum alloy, a titanium alloy, another alloy, an essentially pure metal, or, potentially, a non-metal (e.g., ceramic or polymeric material)) with respect to a given laser peening process. A particular material will have a characteristic maximum stress penetration depth for compressive residual stresses that can be formed therein by the given laser peening process condition, the given laser peening process condition having a set of process parameters associated therewith.

A critical feature of the present invention is that the bar thickness 20 be chosen so as to be at least twice the characteristic maximum stress penetration depth that can be produced within the particular material for the given laser peening process. The reasoning behind this is that the bend bar 10 has a mid-thickness plane 28 relative to bar thickness 20 extending in a direction parallel to the test area or test surface 26. If bar thickness 20 is not large enough, compressive maximum stress penetration depth 30 can then extend beyond mid-thickness plane 28 relative to bar thickness 20. If this situation should occur, the deflection produced in the bend bar 10 can be lower than expected. To explain, those compressive residual stresses which extend past the mid-thickness plane 28 actually would tend to cause unbending of the bar 10 and thereby produce a lower deflection reading than expected.

Laser peening typically produces compressive stresses to a depth of 0.040 to 0.060 inches in steel, but this characteristic depth of penetration may differ somewhat for other alloys and metals processed using the same laser peen processing conditions. The key once again is to choose the bar thickness 20 so as to be at least twice as great as the maximum characteristic compressive residual stress penetration depth that can be achieved within a given material using given laser peening conditions. Using the normal depth of penetration that can be achieved within steel as a general guideline for most metals, bar thickness 20 should be chosen so as to be at least 0.120 inches so as to avoid the introduction of compressive residual stresses past mid-thickness plane 28 of bar thickness 20.

To promote an even greater margin for error relative to the maximum stress penetration depth 30 achievable in any given material, it is advantageous that the bar thickness 20 be in the approximate range of 0.375 inches to 1.0 inches. While there is a critical minimum bar thickness associated with bend bar 10, bar thickness 20 should not be too great. Specifically, as the bar thickness increases, the deflection of the bar for a given laser peening condition decreases, and the less sensitive the magnitude of the bar deflection will be to variation in the laser peening conditions. Accordingly, it may be preferable to employ a bar thickness 20 of about 0.5 inches or less.

Bar length 18 is advantageously chosen so as to facilitate production of a measurable deflection within the bend bar 10 of at least 0.010 inches and preferably in the approximate range of 0.012 inches to 0.018 inches for the selected laser peening conditions. In order to achieve such a measurable deflection in bend bar 10, bar length 18 should be about 4.0 inches to about 12.0 inches and advantageously about 6.0 inches. In fact, a bend bar 10 having a bar length of about 6.0 inches to about 8.0 inches and having a bar thickness 20 of about 0.120 inches to about 0.500 inches tends to provide consistent deflection results and is suitably sensitive to the selected process parameters associated with the laser peening process.

The bar width 22 is advantageously chosen so as to be at least equal to the bar thickness 20 to maintain a stable, consistent deflection orientation normal to the laser peened surface. The maximum width can be selected to be the same as the width of the laser peened area on the surface, or somewhat larger than this if necessary to meet other governing conditions, such as a standardized width or deflection optimization criteria.

The deflection that is achieved with thick strips is progressively lower as the thickness is increased. In situations where the deflection after laser peening is less than about 0.008 inches, the sensitivity of the specimen to minor changes in process parameters is not adequate. Preferably, the deflection reading after laser peening is at least about 0.010 inches and preferably in the 0.012-0.018 inches range. Such a deflection reading can be accomplished by using a longer bend bar 10 so that the deflection at the mid-point of the length thereof is accentuated. In addition, the deflection can be increased somewhat by increasing the relative size of the test area 24 to the test surface 26.

Test area 24 of bend bar 10 includes a spot pattern 32. Spot pattern 32 created by the laser peening is chosen so as to achieve sufficient deflection for processing-sensitive measurements and yet minimize the time required to treat test area 24 of test surface 26. Advantageously, spot pattern 32 is composed of a series of laser spots aligned essentially linearly along a center line 34 of test surface 26. Center line 34 extends in a direction parallel to bar length 18. The laser spots may be applied in a variety of patterns. Spot pattern 32 can be chosen so as to simulate a spot pattern used in an actual application setting. Such spots within the spot pattern 32 may be applied in one or more layers and may or may not be overlapped within one another. In any event, bend bar 10 will have only one test surface 26 upon which a spot pattern 32 is created so as to avoid the possibility of residual stress effects being produced from multiple sides of bend bar 10 and thereby potentially interfering and/or canceling one another out. Such interference/cancellation would reduce the consistency achievable with this quality control method.

Alternatively, it is understood that bend bar 10 may have cross sections which are not necessarily square or rectangular in nature. Other cross sections, either regular (e.g., circular, oval, or polygonal) or irregular, may prove desirable based upon the actual part being simulated within the quality control test. However, it still remains critical that the cross section thickness relative to the test surface be at least twice the maximum stress penetration depth of the compressive residual stresses generated within that particular piece during laser peening thereof. Additionally, it is also advantageous that the bend bar has a length sufficient to promote ready measurement of the deflection created by the compressive residual stresses generated therein by the laser peening process.

A vise fixture 12 is used for holding one end of bend bar 10 rigidly in place during the laser peening operation associated with the quality control test of the present invention. FIG. 4 shows a useful vise fixture 12 for this application. Such a fixture 12 features a pair of V-shaped members 36 slidably moveable and fixably positionable relative to one another via a vise table 38. Such a fixture configuration is able to accommodate a variety of sizes and shapes for bend bar 10. It is also important to note that the method of fixturing is not critical to this invention. The bend bar made be held by one or both ends, in the center, or attached to a backing plate that holds the bend bar flat during laser peening.

Figure 4A:
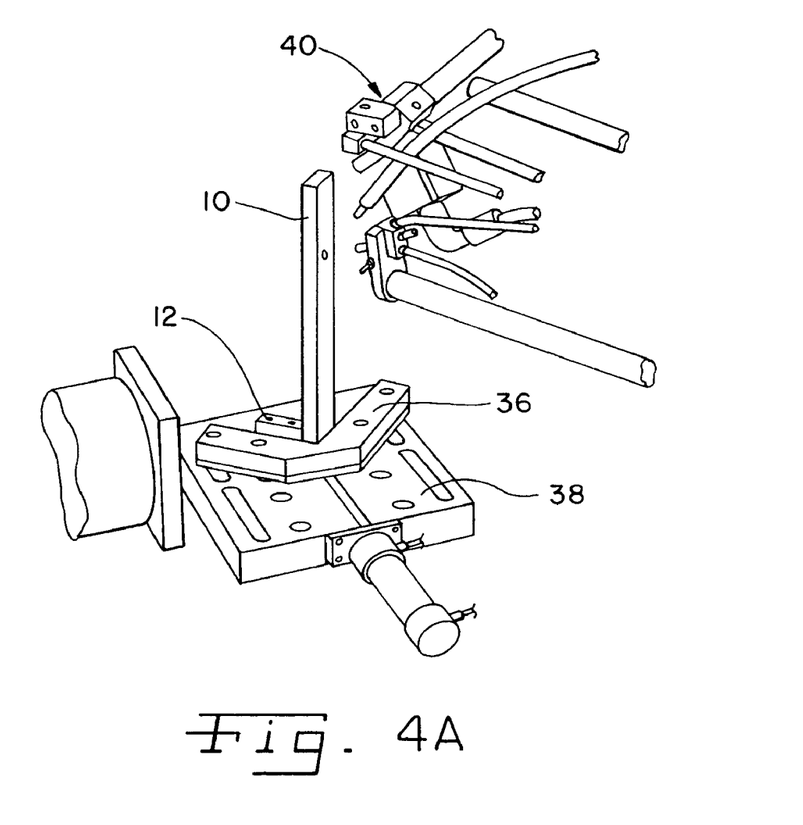
FIGS. 4A and 4B are perspective views of an overlay coating system for use in laser processing of the bend bar of the present invention.
Figure 4B:
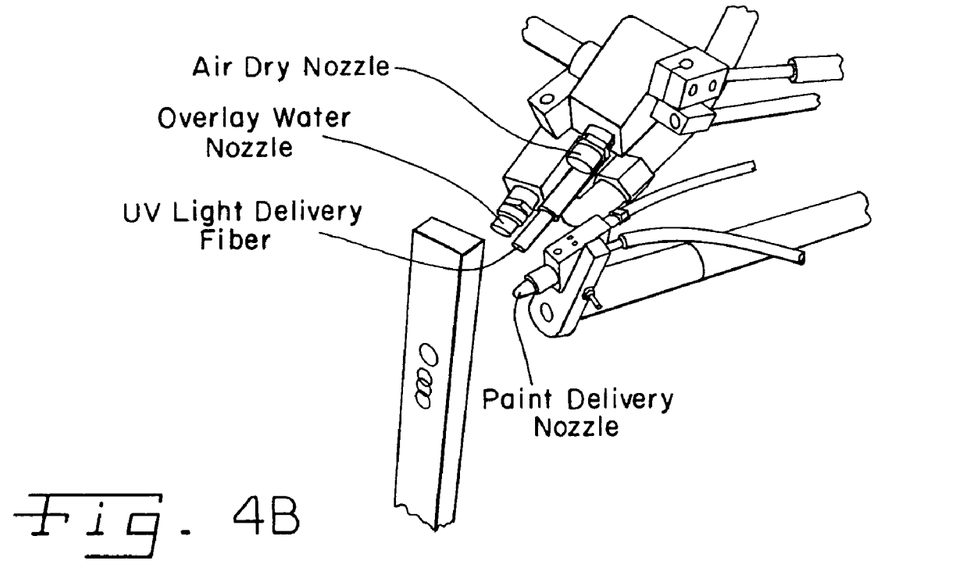

The possible elements and their arrangement in an apparatus for laser peening a bend bar for process monitoring are also shown in FIGS. 4A and 4B. Laser peening apparatus 14 includes a laser mechanism 15 and may include, as shown, transparent overlay applicator 16 and/or an opaque overlay applicator apparatus 40. A general such laser peening system can be found in U.S. Pat. No. 5,741,559 to Jeff Dulaney, assigned to LSP Technologies, Inc. and hereby incorporated by reference. The movement, beam energy, beam firing time, and laser power all can be controlled so as to achieve the desired spot pattern 32 within bend bar 10. A nominal set of conditions for use on bend bar 10 is 40 J, 20 ns, 0.25 cm$^2$ spot area, and/or a power density of about 8 GW/cm$^2$. The laser beam can be directed to different locations so as to create a spot pattern in which the spots are formed in one or more layers of processing and with no overlapping or with controlled overlapping of adjacent spots (e.g., a 30% overlap).

Advantageously, a RapidCoater™ system (combining applicators 16 and 40) is used as the overlay applicator apparatus for applying an energy-absorbing overlay, a transparent overlay, or, optimally both, to test surface 26 of bend bar 10 (one form of which is shown in FIG. 4A, 4B). Such a coating system is able to deliver both a transparent overlay, in the form of water, and an energy-absorbing opaque overlay. The RapidCoater™ system further includes a paint delivery nozzle. An advantage of the RapidCoater™ System is that it represents a miniaturized, compact system for applying the overlay materials during the laser peening process.

Laser peening process parameters that can be controlled using overlay applicator apparatus 40 include, for example, the energy-absorbing/opaque coating selection and the overlay selection and the amount of each thereof to be applied. It is recognized that the opaque coating selection may be in the form of tape, paint, UV-curable coating material, or another appropriate medium. The opaque coating is typically black, but can be any color that absorbs a very high percentage of the laser beam energy. Water is typically used as the transparent overlay material but other substances which are substantially transparent to the laser beam wavelength may be chosen for this purpose if the process situation warrants.

As outlined, there can be a variety of laser peening parameters associated with a given laser peening process. Such parameters can include, but are not necessarily limited to, laser settings such as beam energy, laser power, and laser pulse duration; processing conditions, such as the laser beam spot size and spot pattern; transparent overlay characteristics including the transparent overlay material selection and the thickness and mode thereof to be applied; energy-absorbing/opaque overlay characteristics such as the overlay form (e.g., tape, paint, or coating), overlay composition, and the overlay amount thickness and application mode thereof; and bend bar characteristics such as the bar composition, dimensions, and shape.

Figure 5A:
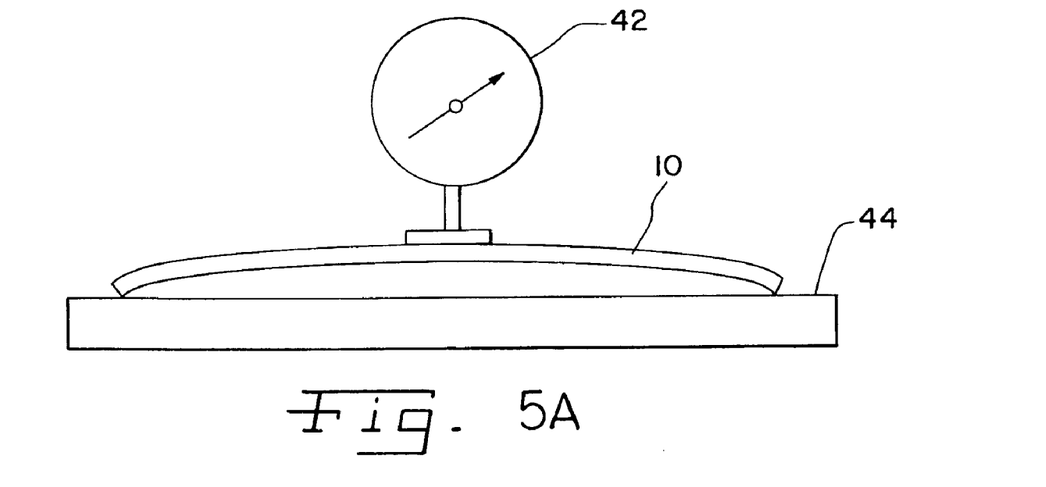
FIGS. 5A and 5B are schematic views of the two methods for measurement of the deflection of a bend bar after laser peening.
Figure 5B:
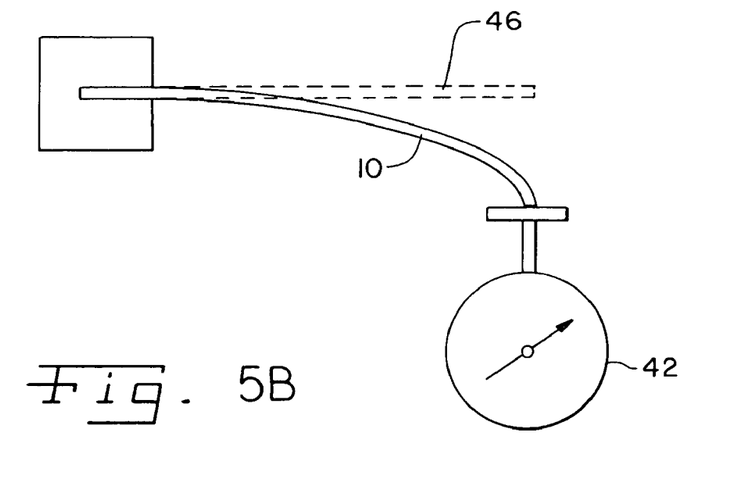

FIGS. 5A and 5B show schematics of two possible methods for measuring the deflection of the bend bar after laser peening. In the first method, the deflection of the center of the bend bar 10 is measured by a measurement device 42 relative to a plane 44 upon which both ends of the bend bar rest. In the other method shown, the deflection of one end of the bend bar 10 from its initial position 46 before laser peening is measured by a measurement device 42. In this method, the laser peening pattern cannot extend out to the ends of the bar, but allowance must be made to not process the length of the end of the bar in the grip holding the bar for measurement. The first method is similar to that used for measuring the deflection in shot peened Almen strips.

Figure 6:
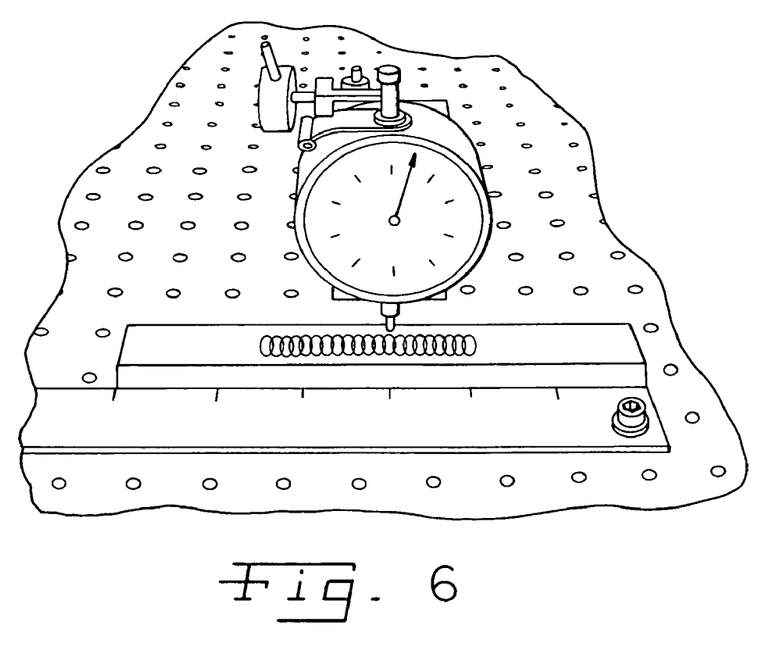
FIG. 6 is a perspective view of a dial indicator gauge set-up for measuring the deflection created in a bend bar of the present invention.
Figure 7:
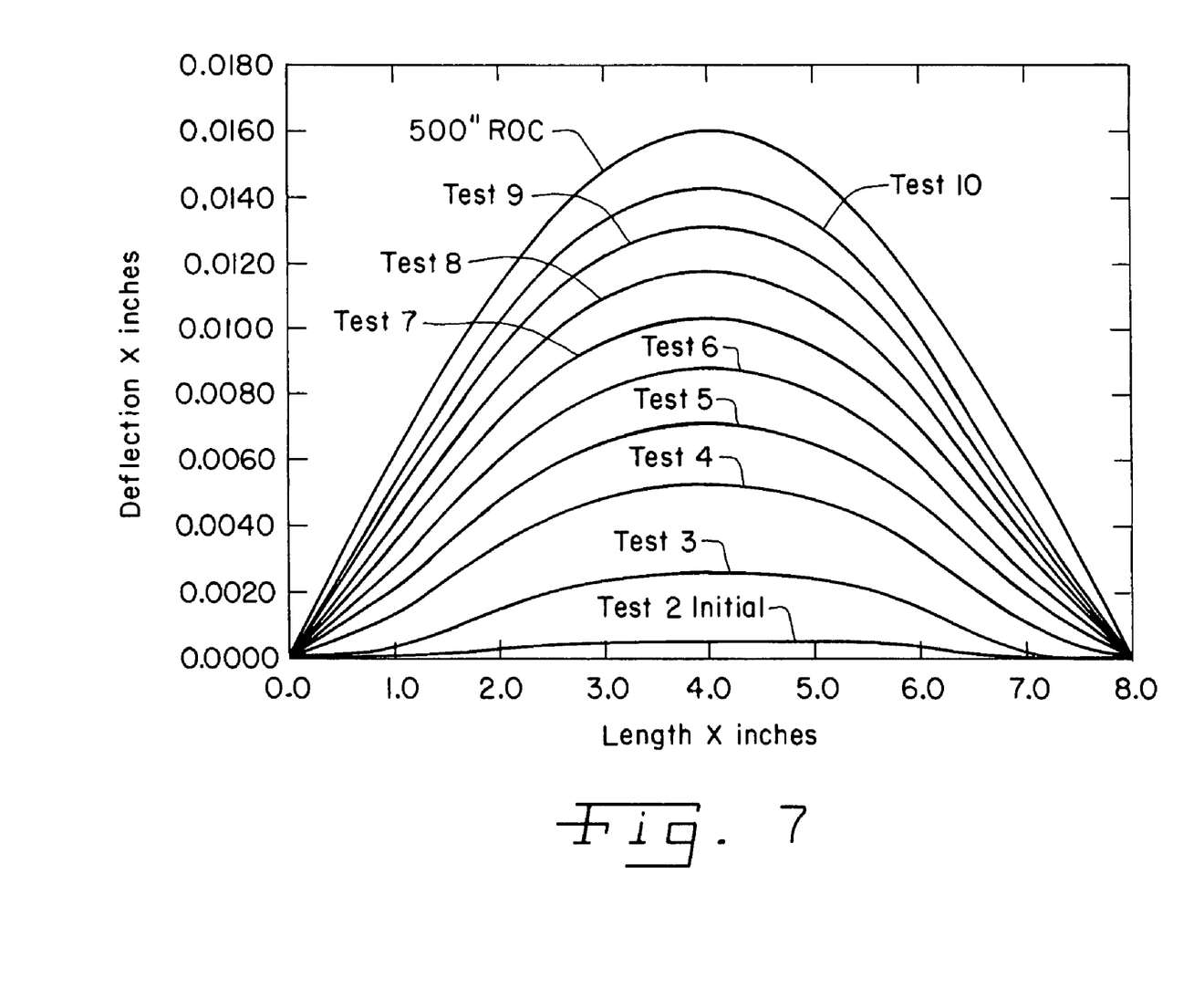
FIG. 7 is a graphical plot of example data for the deflection or bowing of a bend bar along its length thereof for a series of spot applications or tests.

Various instruments are available that are suitable for measuring the deflection generated in the bend bar resulting from the application spot pattern 32 on test surface 26 thereof. A gage mechanism 42 and setup for measuring such deflection or bowing of the middle of the bend bar is shown in FIG. 6. Although FIG. 6 shows an experimental set-up with a mechanical, analogue gage, a gage specifically designed to measure deflections in laser peened test bend bars using an analogue or digital electronic, optical, acoustic or other measurement means could be used. FIG. 7 shows an example bend bar deflection data plot for a series of related laser peening tests, measured as shown in FIG. 6. As seen, the data is plotted in terms of deflection relative to a measurement position along the length 18 of bar 10. As is generally typical for such plots, no matter what the process parameters are, the deflection of the bar from a reference plane upon which both ends of the bar rest, is a minimum at the ends of the bar and reaches a maximum at the mid-point of the length if the laser peened pattern is centered on the width and the length of the bend bar. The deflection produced in the bend bar by laser peening thereof may be measured at any stage of the processing using any suitable type of gage. Optical measurement gauges could be used as a non-contact measurement device during, or after, the peening operation allowing real time measurements of the bar deflection using either of the methods shown in FIGS. 5A and 5B.

In performing the quality control method as a means of representing a laser peening intensity within a particular material, the first step is to select the process parameters to be used for the laser peen apparatus or system 14. Next a test object in the form of bend bar 10 is provided. This bend bar 10 has a bar thickness 20 and a bar length 18 and is composed of the particular material to be tested. This test material has a characteristic maximum penetration depth 30 for compressive residual stresses that can be created by laser peening system 14 when operated using the process parameters selected. The bar thickness 20 is chosen so as to be at least twice characteristic maximum stress penetration depth 30. A test surface 26 is then chosen on bend bar 10, test surface 26 being parallel to the bar length 18 and perpendicular to the bar thickness 20. Upon choosing the test surface 26, spot pattern 32 is laser peened along test surface 26 of bend bar 10. The laser peening is performed using laser peening apparatus or system 14, set to operate under the selected process parameters. The laser peening causes compressive residual stresses to form within bend bar 10, the compressive residual stresses extending from test surface 26 and into bend bar 10. These compressive residual stresses thereby effectively induce bending of bend bar 10, the bending causing a deflection thereof. This deflection is then measured, and this measured deflection can be used as a quality control measurement representing the laser peening intensity within the particular material of which the bend bar 10 is composed.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A quality control method for representing a laser peening intensity within a particular material, the method comprising:
   providing a laser peening system having a plurality of selectable process parameters;
   selecting the process parameters for the laser peening system;
   providing a bend bar comprised of the particular material, the bend bar having:
   (1) a bar length; (2) a characteristic maximum stress penetration depth for compressive residual stresses creatable by laser peening the bend bar using the selected processing parameters; and (3) a bar thickness at least twice the characteristic maximum stress penetration depth;
   choosing a single test surface on the bend bar that is parallel to the bar length and perpendicular to the bar thickness;
   laser peening a spot pattern along the test surface of the bend bar thereby causing compressive residual stresses to form within the bend bar, the compressive residual stresses inducing an out-of-plane deflection of the bend bar;
   measuring the deflection; and correlating the measured deflection to a level of compressive residual stress imparted to the particular material.

2. The method of claim 1, wherein the maximum characteristic stress penetration depth is between about 0.040 inches and about 0.060 inches in steel, and the bar thickness is at least 0.120 inches.

3. The method of claim 1, wherein the bend bar has a mid-thickness plane relative to the bar thickness, the mid-thickness plane extending parallel to the test surface, the bar thickness being at least 0.120 inches to avoid introducing the compressive residual stresses past the mid-thickness plane of the bend bar.

4. The method of claim 1, wherein the bar thickness is in the approximate range of 0.375 inches to 1.0 inch.

5. The method of claim 1, wherein the bar length is sufficient to facilitate production of a measured deflection of at least 0.010 inches.

6. The method of claim 1, wherein the bar length is sufficient to facilitate production of a measured deflection in the approximate range of 0.012 inches to 0.018 inches.

7. The method of claim 1, wherein the bar length is about 4.0 inches to about 12.0 inches.

8. The method of claim 1, wherein the bar length is about 6.0 inches to about 8.0 inches, and the bar thickness is about 0.120 inches to about 0.500 inches.

9. The method of claim 1, wherein the spot pattern is comprised of a series of laser spots aligned linearly along a centerline of the test surface, the centerline extending in a direction of the bar length.

10. The method of claim 1, further comprising:
providing a fixture for holding the bend bar; and
mounting one end of the bend bar in the fixture during laser peening.

11. The method of claim 1, wherein the measuring is performed using at least one of a dial indicator gage, a standard Almen gage, a modified Almen gage, and an optical gage.

12. The method of claim 1, wherein the spot pattern is the same laser peening spot pattern as to be applied to a production component.

13. The method of claim 1, wherein the spots applied to the laser peening spot pattern do not overlap each other.

14. The method of claim 1, wherein the spot pattern does not cover the entire width of the bend bar.

15. The method of claim 14, wherein the distance between the edge of the laser peening spot pattern and the edge of the bend bar is in the range of one half a laser spot diameter to three laser beam spot diameters.

16. The method of claim 1, wherein the spot pattern does not cover the entire length of the bend bar.

17. The method of claim 1, wherein the measurement is made about at the middle of the length of the bend bar.

18. The method of claim 1, wherein the measurement is made at one end of the length of the bend bar while gripping an end opposite thereto.

19. A quality control method for representing a laser peening intensity within a workpiece, the workpiece being comprised of a workpiece material, the method comprising:
providing a laser peening system having process parameters associated therewith;
providing a bend bar comprising: (i) a test material that is substantially the same as the workpiece material, the test material having a characteristic maximum stress penetration depth for compressive residual stresses creatable by laser peening the test material using the process parameters; (ii) a bar thickness at least twice the characteristic maximum stress penetration depth; (iii) a bar length; and (iv) a test surface which is parallel to the bar length and perpendicular to the bar thickness;
laser peening a spot pattern along the test surface thereby causing compressive residual stresses to form within the bend bar, the compressive residual stresses inducing out-of-plane deflection of the bend bar;
measuring the deflection of the bend bar;
correlating the measured deflection to a depth of compressive residual stresses imparted to the test material under the process parameters.

20. The method of claim 19, wherein the laser peening system includes a laser and at least one overlay applicator, each said overlay applicator being configured to supply at least one of a transparent overlay and an energy-absorbing overlay.

* * * * *